(12) United States Patent
Osborne

(10) Patent No.: US 8,337,545 B2
(45) Date of Patent: Dec. 25, 2012

(54) WOVEN IMPLANTABLE DEVICE

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1384 days.

(21) Appl. No.: 11/403,463

(22) Filed: Apr. 12, 2006

(65) Prior Publication Data

US 2006/0235511 A1    Oct. 19, 2006

Related U.S. Application Data

(63) Continuation-in-part of application No. 11/054,043, filed on Feb. 9, 2005.

(60) Provisional application No. 60/542,922, filed on Feb. 9, 2004, provisional application No. 60/670,716, filed on Apr. 13, 2005.

(51) Int. Cl.
    A61F 2/06    (2006.01)
(52) U.S. Cl. .................. 623/1.24; 623/2.42; 623/2.14
(58) Field of Classification Search ............ 623/1.24, 623/1.26, 1.38, 1.44, 1.49–1.54
    See application file for complete search history.

(56) References Cited

U.S. PATENT DOCUMENTS

| | | | |
|---|---|---|---|
| 3,063,967 A | 11/1962 | Schultz | |
| 3,063,968 A | 11/1962 | Schultz | |
| 3,169,945 A | 2/1965 | Hostettler et al. | |
| 3,391,126 A | 7/1968 | Baggett et al. | |
| 3,589,392 A | 6/1971 | Meyer | |
| 3,912,692 A | 10/1975 | Casey et al. | |
| 4,218,782 A | 8/1980 | Rygg | |
| 4,272,854 A | 6/1981 | Bokros | |
| 4,665,906 A | 5/1987 | Jervis | |
| 4,731,074 A | 3/1988 | Rousseau et al. | |
| 4,759,759 A | 7/1988 | Walker et al. | |
| 4,863,467 A | 9/1989 | Bokros | |
| 4,872,875 A | 10/1989 | Hwang | |
| 4,902,508 A | 2/1990 | Badylak et al. | |
| 4,923,465 A | 5/1990 | Knoch et al. | |
| 4,952,215 A | 8/1990 | Ouriel et al. | |
| 5,080,670 A | 1/1992 | Imamura et al. | |
| 5,108,425 A | 4/1992 | Hwang | |
| 5,178,632 A | 1/1993 | Hanson | |
| 5,192,313 A | 3/1993 | Budd et al. | |
| 5,275,826 A | 1/1994 | Badylak et al. | |
| 5,281,422 A | 1/1994 | Badylak et al. | |
| 5,282,824 A | 2/1994 | Gianturco | |
| 5,370,685 A | 12/1994 | Stevens | |
| 5,376,113 A | 12/1994 | Jansen et al. | |
| 5,411,552 A | 5/1995 | Andersen et al. | |
| 5,489,297 A | 2/1996 | Duran | |
| 5,500,014 A | 3/1996 | Quijano et al. | |
| 5,522,841 A | 6/1996 | Roby et al. | |
| 5,711,969 A | 1/1998 | Patel et al. | |
| 5,713,920 A | 2/1998 | Bezwada et al. | |

(Continued)

*Primary Examiner* — David Isabella
*Assistant Examiner* — Suba Ganesan
(74) *Attorney, Agent, or Firm* — Buchanan Nipper

(57) ABSTRACT

A prosthetic valve device, a method for making a valve device, and a method for implanting a valve device into a recipient are provided. The valve device includes at least one flexible member formed at least partially from a woven layer. The woven layer includes a first material and a second material being at least partially woven together. The at least one flexible member is movable between a first position that permits fluid flow in a first direction and a second position that substantially prevents fluid flow in a second direction. The valve has a first, unexpanded configuration and a second, expanded configuration.

18 Claims, 6 Drawing Sheets

U.S. PATENT DOCUMENTS

| | | |
|---|---|---|
| 5,713,950 A | 2/1998 | Cox |
| 5,725,572 A | 3/1998 | Lam et al. |
| 5,733,337 A | 3/1998 | Carr, Jr. et al. |
| 5,741,327 A | 4/1998 | Frantzen |
| 5,840,081 A | 11/1998 | Andersen et al. |
| 5,855,601 A | 1/1999 | Bessler et al. |
| 5,885,619 A | 3/1999 | Patel et al. |
| 5,955,110 A | 9/1999 | Patel et al. |
| 5,957,949 A | 9/1999 | Leonhardt et al. |
| 5,968,096 A | 10/1999 | Whitson et al. |
| 6,015,431 A | 1/2000 | Thornton et al. |
| 6,022,374 A | 2/2000 | Imran |
| 6,117,979 A | 9/2000 | Hendriks et al. |
| 6,126,686 A | 10/2000 | Badylak et al. |
| 6,146,416 A | 11/2000 | Andersen et al. |
| 6,168,614 B1 | 1/2001 | Andersen et al. |
| 6,200,336 B1 | 3/2001 | Pavcnik et al. |
| 6,206,931 B1 | 3/2001 | Cook et al. |
| 6,280,467 B1 | 8/2001 | Leonhardt |
| 6,287,335 B1 | 9/2001 | Drasler et al. |
| 6,299,637 B1 | 10/2001 | Shaolian et al. |
| 6,312,474 B1 | 11/2001 | Francis et al. |
| 6,375,989 B1 | 4/2002 | Badylak et al. |
| 6,379,710 B1 | 4/2002 | Badylak |
| 6,440,164 B1 | 8/2002 | DiMatteo et al. |
| 6,444,229 B2 | 9/2002 | Voytik-Harbin et al. |
| 6,458,153 B1 | 10/2002 | Bailey et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,572,650 B1 | 6/2003 | Abraham et al. |
| 6,582,462 B1 | 6/2003 | Andersen et al. |
| 6,585,761 B2 | 7/2003 | Taheri |
| 6,602,286 B1 * | 8/2003 | Strecker ................ 623/1.24 |
| 6,666,886 B1 | 12/2003 | Tranquillo et al. |
| 6,685,739 B2 | 2/2004 | DiMatteo et al. |
| 6,705,585 B1 | 3/2004 | Roy |
| 6,730,118 B2 | 5/2004 | Spenser et al. |
| 6,752,828 B2 | 6/2004 | Thornton |
| 2001/0007956 A1 | 7/2001 | Letac et al. |
| 2001/0011187 A1 | 8/2001 | Pavcnik et al. |
| 2001/0039450 A1 | 11/2001 | Pavcnik et al. |
| 2002/0099439 A1 | 7/2002 | Schwartz et al. |
| 2002/0123800 A1 | 9/2002 | Taheri |
| 2002/0138135 A1 | 9/2002 | Duerig et al. |
| 2002/0188348 A1 | 12/2002 | DiMatteo et al. |
| 2003/0055492 A1 | 3/2003 | Shaolian et al. |
| 2003/0083741 A1 | 5/2003 | Woo et al. |
| 2003/0093071 A1 | 5/2003 | Hauck et al. |
| 2003/0125795 A1 | 7/2003 | Pavcnik et al. |
| 2003/0130726 A1 | 7/2003 | Thorpe et al. |
| 2003/0153972 A1 | 8/2003 | Helmus |
| 2003/0171824 A1 | 9/2003 | Abraham et al. |
| 2003/0191525 A1 | 10/2003 | Thornton |
| 2003/0195618 A1 | 10/2003 | Abraham et al. |
| 2003/0208261 A1 | 11/2003 | Thorpe et al. |
| 2003/0209835 A1 | 11/2003 | Chun et al. |
| 2003/0236568 A1 | 12/2003 | Hojeibane et al. |
| 2004/0024452 A1 | 2/2004 | Kruse et al. |
| 2004/0049266 A1 | 3/2004 | Anduiza et al. |
| 2004/0073297 A1 | 4/2004 | Rohde et al. |
| 2004/0098112 A1 | 5/2004 | DiMatteo et al. |
| 2004/0137042 A1 | 7/2004 | Hiles et al. |
| 2004/0167619 A1 | 8/2004 | Case et al. |
| 2004/0180042 A1 | 9/2004 | Cook et al. |
| 2004/0186558 A1 | 9/2004 | Pavcnik et al. |
| 2004/0210301 A1 | 10/2004 | Obermiller |
| 2004/0225352 A1 | 11/2004 | Osborne et al. |
| 2005/0143807 A1 | 6/2005 | Pavcnik et al. |
| 2005/0267560 A1 | 12/2005 | Bates |
| 2006/0111770 A1 | 5/2006 | Pavcnik et al. |

\* cited by examiner

WOVEN IMPLANTABLE DEVICE

RELATED APPLICATIONS

This application is a continuation-in-part of U.S. application Ser. No. 11/054,043, filed Feb. 9, 2005, which claims priority to U.S. Provisional Application Ser. No. 60/542,922, filed Feb. 9, 2004, which are incorporated by reference herein in their entirety. This application also claims priority to U.S. Provisional Application Ser. No. 60/670,716, filed Apr. 13, 2005, which is incorporated by reference herein in its entirety.

FIELD OF THE INVENTION

This invention relates to woven materials for medical devices, and in particular to prosthetic valve devices and methods of making such devices.

BACKGROUND

By use of a closed circulatory system, animal bodies use many internal organs and vessels to transport fluids from one bodily location to another. Components of the circulatory system include the heart, blood vessels, and blood. The heart has valves (semilunar valves and atrioventricular valves) that regulate the flow of blood in the atria and the ventricles. Three examples of blood vessels are arteries, veins, and capillaries. Whereas arteries transport blood to organs throughout the body (i.e., away from the heart), veins carry blood back to the heart. Structurally, capillaries have an inner endothelium surrounded by a membrane, while arterial and venal walls have three layers: connective tissue forms the outer layer, while smooth muscle having elastic fibers forms the middle layer, and there is an innermost endothelial layer. Mammalian veins, such as human veins for example, have naturally occurring valves positioned along the length of the vessel.

Mammalian valves, such as human venous valves for example, act as one-way check valves that open to permit the flow of a fluid in a first direction (e.g., muscles contract, squeeze the veins, and the valves—flaps of tissue—keep blood moving toward the heart), and quickly close upon a change in pressure or when muscles relax or stop contraction, to substantially prevent fluid flow in a reverse direction, i.e., retrograde flow.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of valve leaflets to close. Furthermore, the leaflets may become damaged, such as by formation of thrombus and scar tissue, which may also affect the ability of the valve leaflets to close. Once valves are damaged, venous insufficiency may be present and can lead to discomfort and possibly ulcers in the legs and ankles.

Current treatments for venous insufficiency include the use of compression stockings that are placed around the leg of a patient in an effort to force the vessel walls radially inward to restore valve function. Surgical techniques are also employed in which valves can be bypassed, repaired or replaced with autologous sections of veins with competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990s. Prosthetic valves that mimic the function of natural valves have been shown to be helpful in treating venous insufficiency.

Prosthetic valves generally include a plurality of leaflets that control the flow of fluid through the valve. One problem with the leaflets of the prosthetic valves currently being made occurs with remodeling of the leaflets where the leaflets adhere to the vessel wall or the leaflets contract to the point where coaptation of the leaflets is impossible. These remodeled leaflets no longer function to control the fluid through the valve. Woven compositions of the present invention provide additional structure using woven materials to help maintain the ability of the leaflets of the prosthetic valve device to continue to be moveable to control the fluid flow through the prosthetic valve device. Therefore, it is desirable to have woven structures and prosthetic valve devices formed from a woven structure for implantation in a body vessel and methods of making such devices as taught herein.

BRIEF SUMMARY

In one embodiment of the present invention, a prosthetic valve device for implantation into a body vessel is provided. The valve device includes at least one flexible member formed at least partially from a woven layer. The woven layer includes a first material and a second material being at least partially woven together. The at least one flexible member is movable between a first position that permits fluid flow in a first direction and a second position that substantially prevents fluid flow in a second direction. The valve has a first, unexpanded configuration and a second, expanded configuration.

In another embodiment of the present invention, a method of making a prosthetic valve for implantation into a body vessel is provided. The method includes providing a first material and providing a second material, weaving together at least a portion of the first material with the second material to form a woven layer; and forming a valve device from the woven layer. The first material is capable of forming a first, unexpanded configuration and a second, expanded configuration for the woven layer.

In another embodiment of the present invention, a method of implanting a prosthetic valve into a body vessel is provided. The method includes providing a valve having at least one flexible member formed at least partially from a woven layer. The woven layer includes a first material and a second material that are at least partially woven together. The at least one flexible member is movable between a first position that permits fluid flow in a first direction and a second position that substantially prevents fluid flow in a second direction, the woven comprising a woven layer. The method further includes delivering the prosthetic valve in a first, unexpanded configuration through the body vessel to an implantation site and implanting the valve in a second, expanded configuration.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE INVENTION

The present invention relates to medical devices, and in particular to prosthetic valves with inflatable frames for implantation in a body vessel, preferably a vascular vessel, methods of making such valves, and delivery systems for such valves to a body vessel. For example, the valves of the present invention are suitable for implantation into the vessels of the vasculature, such as veins, for regulating fluid flow through the vessel. The valves of the present invention may also be implanted in a passageway of the heart to regulate the fluid flow into and out of the heart. As used herein, the term "implantable" refers to an ability of a medical device to be positioned at a location within a body, such as within a body vessel, either temporarily, semi-permanently, or permanently. Permanent fixation of the valve device in a particular position is not required. Furthermore, the terms "implantation" and "implanted" refer to the positioning of a medical device at a location within a body, such as within a body vessel.

For the purposes of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, contain(s) and the variants thereof are intended to be open ended transitional phrases, terms, or words that do not preclude the possibility of additional steps or structures.

Figure 1:
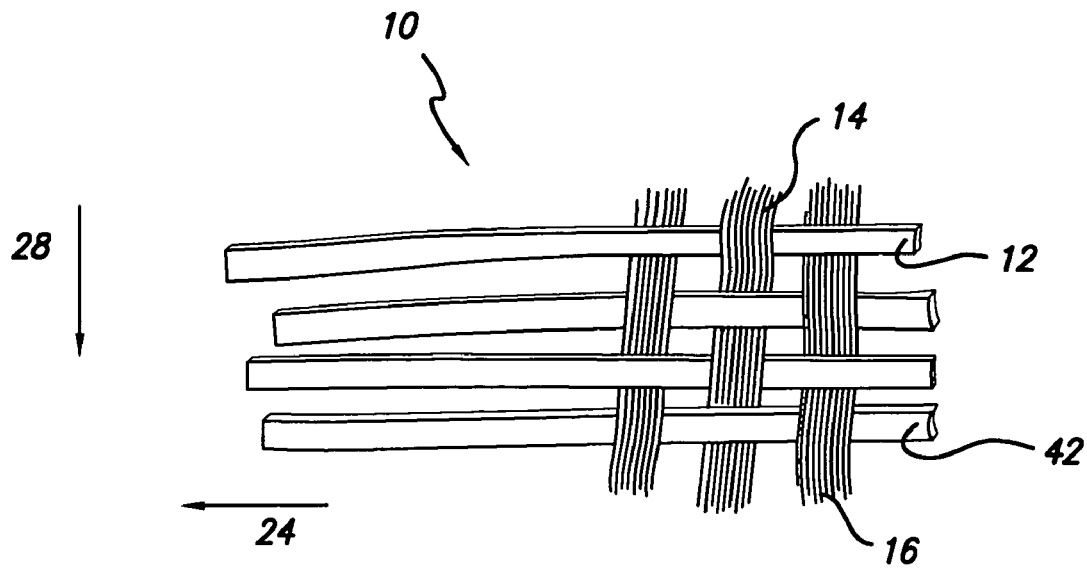
FIG. 1 illustrates an embodiment of the woven structure of the present invention.

An embodiment of a woven structure 10 of the present invention is shown in FIG. 1. The woven structure 10, as shown in FIG. 1 includes a first material 12 at least partially woven together with a second material 14. In some embodiments, the first material 12 provides support for the second material 14. Additionally, the first material 12 may be used to provide several configurations, including a first, unexpanded configuration and a second, expanded configuration for the woven structure 10 as will be described in more detail below with reference to a prosthetic valve. The first material may provide a stenting function, i.e., exerts a radially outward force on the interior of the implantation site that may be used as a frameless valve. Alternatively, the first material 12 may provide support for the second material 14 and may be connected to a frame, such as a stent. The woven structure 10 may be sized and shaped in multiple configurations depending on several factors, including the nature of the location for placement of the woven structure 10 within a patient. The woven structure 10 will be woven of materials selected depending on several factors, including, but not limited to the size and shape of the valve device, and the location and size of the body site, the flow velocity of fluid through the body site, the proximity of other valves, both competent and incompetent, and the function of the woven structure 10. The first material 12 and the second material 14 may be the same materials or different materials as described in more detail below.

In some embodiments, the woven structure 10 may be formed on a loom using the first material 12 and the second material 14 for the warp, the weft, or both. The warp refers to the material running in the lengthwise direction of a woven structure and the weft refers to the material running perpendicular to the warp. The weaving pattern and the flexibility of the woven structure may be modified by materials used for the warp and the weft, the amount of tension placed on the individual materials, such as fibers, as the material are woven together, and the like. Preferably, the weaving pattern is programmable and may include additional factors such as the shape of the woven structure and the ply of the woven structure formed. The ply of the woven structure may be single ply wherein a single fiber is used in the warp and the weft or double ply wherein two fibers are twisted together to form a thread that is used in the warp and the weft. Additional plys and combinations of plys may be used with the present invention. The woven structure 10 may be woven using an industrial loom suitable for making medical grade products. Preferably the loom is programmable with respect to the weave pattern and the shape of the woven structure 10. Woven medical products using an industrial loom are commercially available, for example at Bally Ribbon Mills, Bally, Pa. Any method known to one skilled in the art for forming a woven structure may be used with the present invention.

As shown in FIG. 1, the first material 12 and the second material 14 are woven together to form a mesh 16. As will be understood by one of skill in the art, the mesh 16 may be formed in many different combinations of the first material 12 and the second material 14, and the mesh 16 may include additional materials as described below. The mesh 16 may be formed from a uniform weave of the first material 12 and the second material 14 as shown in FIG. 1 where the first material 12 is aligned in a first direction 24 and the second material 14 is aligned in a second direction 28.

As will be understood by one of skill in the art, many alternative weaving patterns may be used with the present invention. For example, the ratio of the first material 12 to the second material 14 may vary, i.e. in a range of ratios from 1:10 to 10:1 of the first material 12 to the second material 14 over the entire woven structure 10 or, alternatively, over a portion of the woven structure 10. The materials 12 and 14 may be aligned in the first direction 24, the second direction 28 or both. The weave pattern may be uniform, including repetitive patterns, or the weave pattern may be non-uniform.

Figure 2:
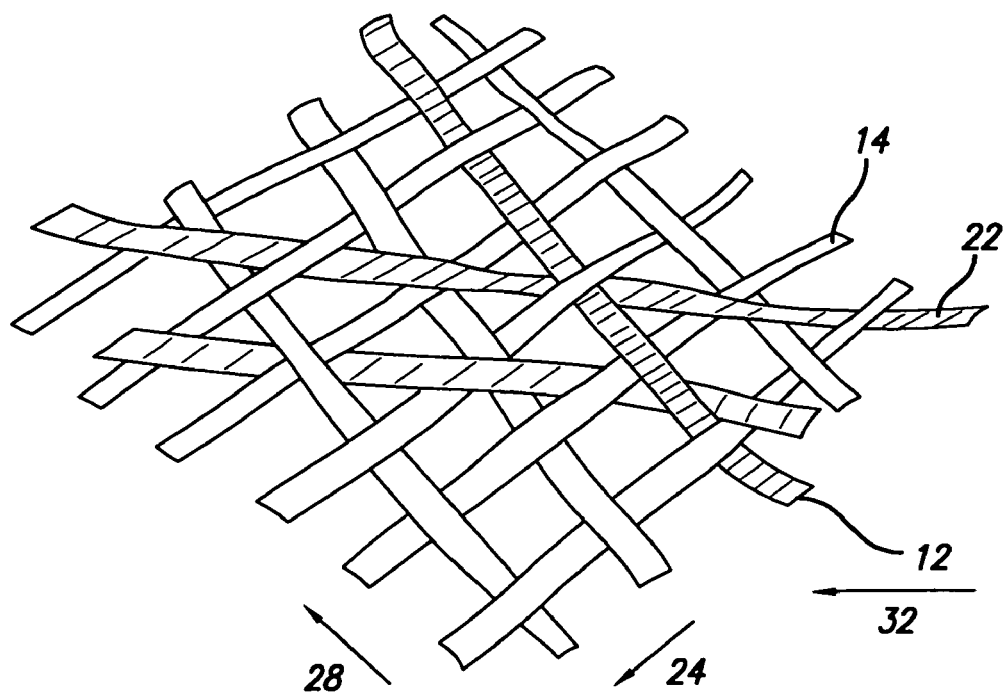
FIG. 2 illustrates an alternative weave pattern of the embodiment shown in FIG. 1.

The woven structure 10 of the present invention may also be formed form an irregularly woven pattern as shown in FIG. 2. The first material 12 and the second material 14 may be irregularly positioned and woven together in multiple directions including the first direction 24 and the second direction 28 as well as a third direction 32 as shown in FIG. 2 as diagonally woven. Non-uniform weaving of the woven structure 10 may include a high percentage of the second material, i.e. 80-100% in one area such as near an opening as described below and have a different percentage of the second material near the edges of the woven structure 10. Other irregular weaves are possible as will be understood by one of skill in the art.

Figure 3:
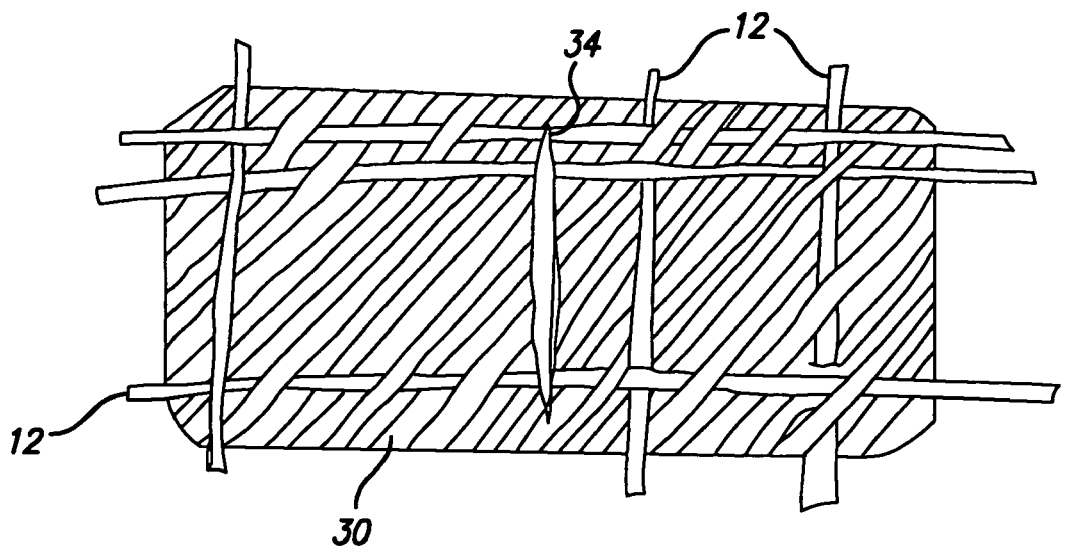
FIG. 3 illustrates an alternative embodiment of the present invention.

As shown in FIG. 3, the first material 12 may be woven through a sheet 30 of the second material 14. The sheet 30 may include an opening 34. The first material 12 may be woven through the sheet 30 of the second material 14 in multiple directions, including, but not limited to the first direction 24, the second direction 28, and the third direction 32. As described below, the sheet 30 may be reformed into alternative shapes and sizes to be at least partially woven together with the first material 12.

Figure 4:
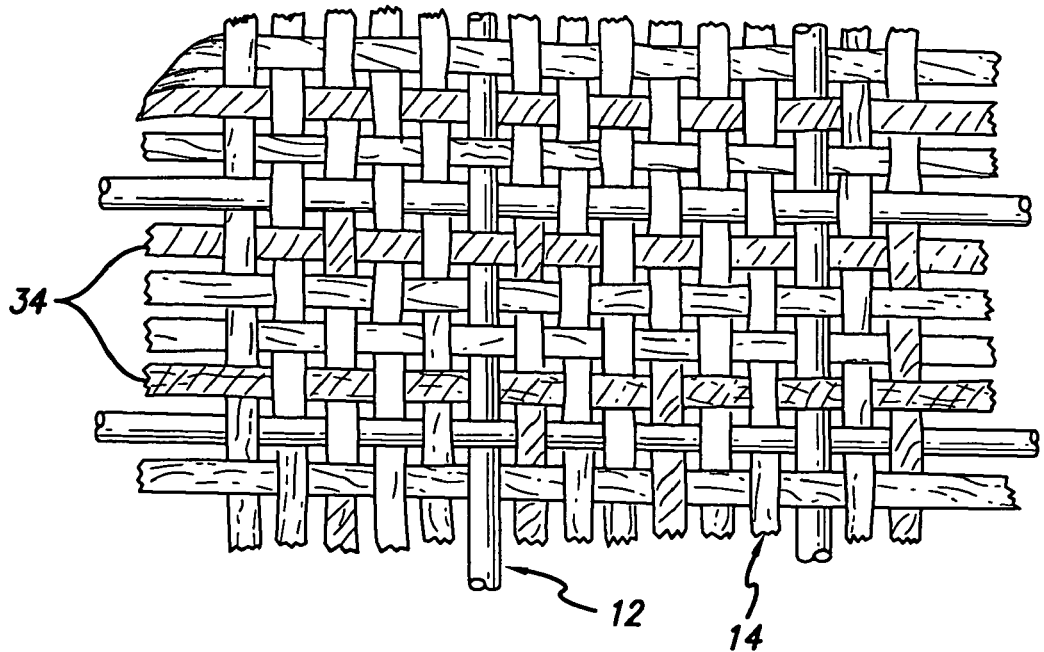
FIG. 4 illustrates an embodiment of the present invention having first, second and third material.

FIG. 4 illustrates the woven structure 10 at least partially woven together with the first material 12, the second material 14 and a third material 34. As described above, the woven structure 10 may be woven together using the materials 12, 14, 34 in a uniform pattern or the woven structure 10 may be woven together using the materials 12, 14, 34 in a non-uniform pattern.

In some embodiments, the woven structure 10 includes extensions 42 of the first material 12 that extend beyond a perimeter 40 of the woven structure 10. Extensions 42 of the first material 12 may be used for maintaining the woven structure 10 in position following implantation into the patient. The extensions 42 may be anchoring features such as barbs or hooks or any anchoring feature known to one of skill in the art. Exemplary anchoring features are described in WO 04/089253A1 which is incorporated by reference herein in its entirety. In addition, anchoring features may be added to the extensions 42 by suitable attachment means and techniques, such as welding and bonding. Formation of the woven structure 10 into a prosthetic valve device will be discussed below.

The woven structure 10 may be used to form a prosthetic valve device 100, 200 as shown in FIGS. 5-9. The valve device 100 may be formed from the woven structure 10 using the first material 12 and the second material 14 at least partially woven together. The materials 12 and 14 may be woven and then formed in to the shape of the valve 100, 200. Alternatively, the material 12, the material 14 or both may be woven into the shape of valve 100, 200 directly. In some embodiments, the first material 12 may be formed in the shape of the valve device 100, 200 for delivery to a vessel wall, for example, using a mandrel to establish a memory shape. The second material 14 and any additional materials when at least partially woven together with the first material 12 conform to the shape, of the material 12. In some embodiments, the first material 12 may be woven and formed into the shape of the valve device 100, 200 and then coated with the second material 14, thereby interweaving the second material 14 between the woven first material 12 as the first material 12 is being coated, for example when using THORALON or liquefied SIS as the second material 14. The valve device 100 may be radially collapsed for delivery by a catheter to a location within a body vessel. Once in position at the location, the valve 100 may be radially expanded to the memory shape to function as a valve in the body vessel.

Figure 6A:
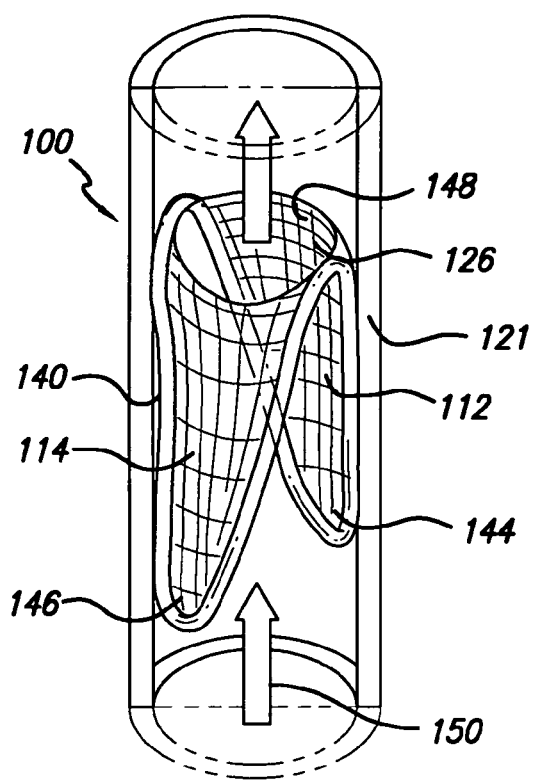
FIG. 6A illustrates the valve device of FIG. 5 in a vessel wall is an open position.

For example, shape memory alloys (described below) may be used that provide advantages during delivery of the valve to the implantations site and also to bias the leaflet open or closed. The shape memory alloy may be woven into the desired shape, such as a leaflet and heat treated. When an alloy such as nitinol is used, the alloy is characterized by long-term stability under cyclic loading, and its temperature lies below the normal body temperature. Below the transition temperature range, the memory alloy is in a martensitic state and the device has a linear or collapsed configuration. Above the martensitic transition temperature range, the alloy is transformed to an austentic state, recovering the shape which it received during heat treatment. Thus, the valve 100 including the shape memory alloy may be inserted into the vessel in the collapsed position and assume the memory shape as the alloy warms to body temperature. The alloy may also be shaped to form leaflets that are biased toward the closed position (i.e. as shown in FIG. 6B) or to the open position (i.e. as shown in FIG. 6A) where the leaflets assume the memory shape as the alloy warms to body temperature.

Figure 5A:
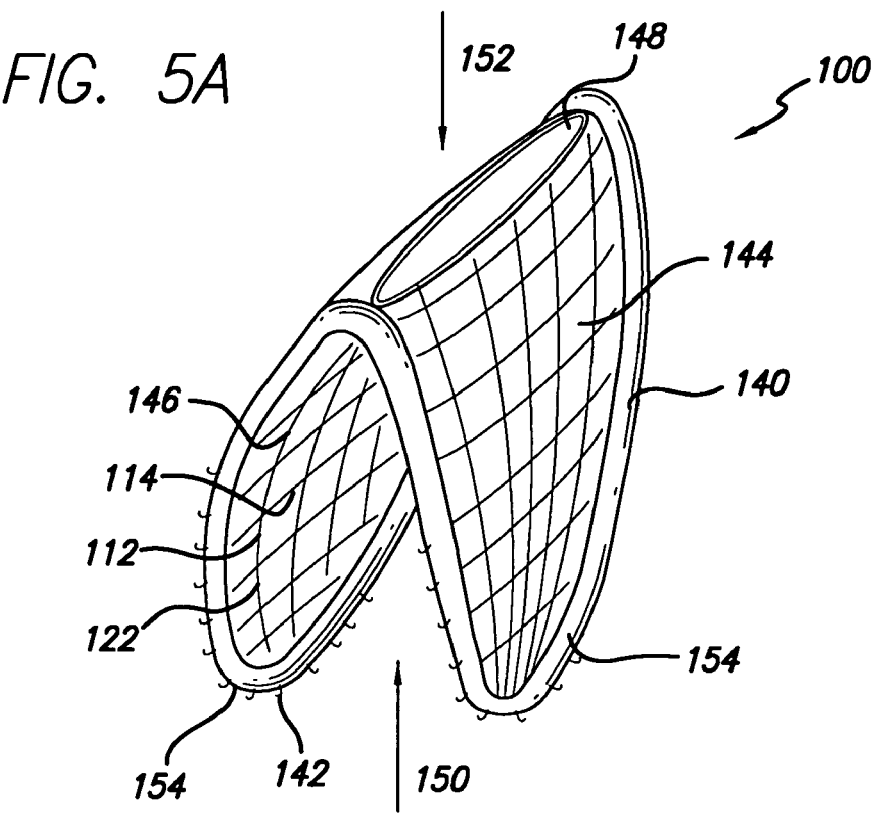
FIG. 5A illustrates an embodiment of a valve device of the present invention in an expanded configuration.
Figure 5B:
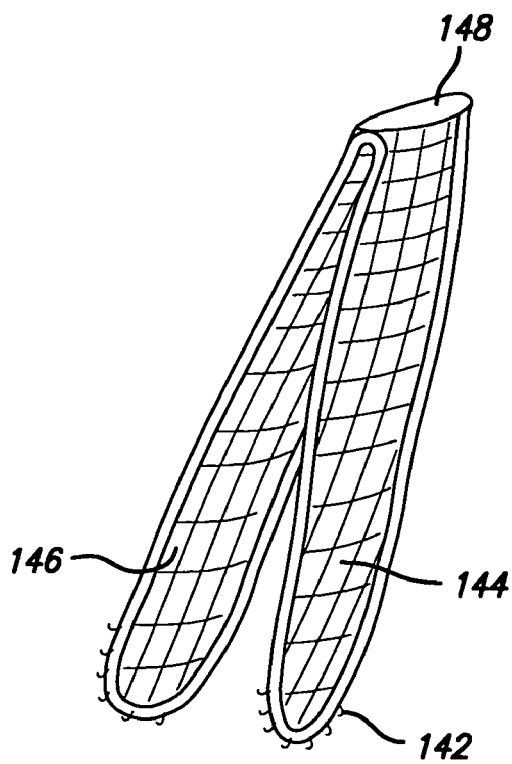
FIG. 5B illustrates the valve device shown in FIG. 5A in an unexpanded configuration.

As illustrated in FIGS. 5A and 5B, the prosthetic valve device 100 of an embodiment of the present invention includes the woven structure 10 having a structure perimeter 140, a first leaflet 144, and an opening 148 in the woven structure 10. FIG. 5A illustrates the expanded configuration for the valve device 10 and FIG. 5B illustrates the unexpanded configuration. Preferably, the structure perimeter 140 is formed by the edge of the materials 12, 14, more preferably, the structure perimeter 140 is formed from the first material 12 to provide a memory shape for the valve device 100 without having an additional frame structure. Alternatively, the structure perimeter 140 may be connected to a support structure, such as a frame, as described below. The opening 148 allows fluid flow in a first direction 150 through the valve device 100 and closure of the opening 148 substantially restricts fluid flow in a second, generally opposite flow direction 152. The valve device 100 further includes extensions 142 of the first material 12 from a portion of the perimeter 140. The extensions 142 may further include barbs or hooks as described above for implanting the valve device 100 in a vessel wall of the recipient.

The embodiment shown in FIGS. 5A and 5B preferably includes the first leaflet 144 and a second leaflet 146. One of skill in the art will understand that the valve device 100 may include one leaflet, or a plurality of leaflets, e.g. two, three, four, five or more leaflets, within the scope of the present invention. The leaflets 144 and 146 may be formed with a flexible material and move outwardly to open the opening 148 when subjected to fluid flow in the first direction 150 in a vessel 121 of the recipient as shown in FIG. 6A, and move inwardly to close the opening 148 when subjected to fluid flow in the second direction 152 in the vessel 121 as shown in FIG. 6B. For example, the woven structure 10 may be formed using a higher percentage of the second material 14 compared to the first material 12 near the opening 148 of the valve device 100. Having a higher percentage of the second material 14 may provide greater flexibility of the leaflets 144, 146 to open and close as the fluid flows through the opening 148. The first material 12 may be used at a greater percentage close to the perimeter 140 to give support for the valve device 100. Preferably, the leaflets 144, 146 may be shaped and sized to provide a sufficient leaflet contact area 158 to decrease the amount of retrograde flow in the vessel as compared to damaged valves as shown in FIG. 6B.

Figure 6B:
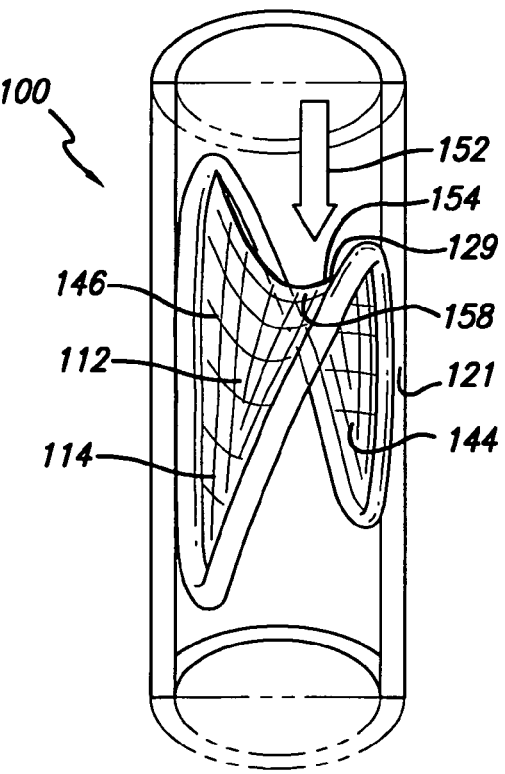
FIG. 6B illustrates the valve device of FIG. 5 in a closed position.

The leaflets 144, 146 contact each other at the leaflet contact area 158 at a proximal portion 129 of the valve device 100, shown in FIG. 6B. The leaflet contact area 158 comprises a longitudinal portion along the valve device 100 in which the facing surfaces of leaflets 144, 146 coapt or lie in close proximity to one another. Preferably, the leaflets 144, 146 may be shaped and sized to provide a sufficient leaflet contact area 158 to decrease the amount of retrograde flow in the vessel 121 as compared to damaged valves. One of skill in the art will understand how to maximize the leaflet contact area 158, for example, but not limited to, lengthening the leaflets 144, 146 longitudinally with respect to the diameter of the vessel 121 into which the valve device 100 is implanted. Preferably, by extending the leaflet contact area 158, the valve device 100 will seal during retrograde flow in the direction 152 so that undesired retrograde flow may be minimized. Prosthetic valves with smaller areas of coaptation make it more difficult for valve leaflets to engage one another and, hence, for the prosthetic valve to seal during retrograde flow. Alternatively, when the valve device 100 is formed with a single leaflet, the leaflet contact area 158 contacts the wall of the vessel 121 to substantially prevent flow in the second direction 152. As described above, the percentage of the first material 12 may be greater near the leaflet contact area 158 at the opening 148 for greater flexibility and for meeting with the vessel wall 121.

Preferably, the leaflets 144, 146 may be sized and shaped so that regular contact the outer walls of the vessel 121 may be diminished, especially when the leaflets 144, 146 are formed from a remodelable material, such as an ECM, which can partially adhere to the wall of the vessel 121 over time as tissue grows into the leaflets 144, 146, thus compromising the functionality of the valve device 100. Remodelable materials, such as ECM, may also retract during remodeling as described below. Inclusion of the first material 12 to shape the leaflets 144, 146 may also help diminish undesired retraction of the leaflets 144, 146 during remodeling. In some embodiments, the leaflets 144, 146 may be formed from the woven structure 10 wherein a portion of a proximal portion 154 of the leaflets 144, 146 include the first material 12 shaped to curve away from the wall of the vessel 121 to help the leaflet contact are remain flexible and nonadherent. The first material 12 may also be provided to shape the leaflets 144, 146 to be biased open such that the retrograde flow pushes the leaflets together and closes the opening 148. Alternatively, the leaflets 144, 146 may be shaped by the first material 12 to be biased closed such that flow in the first direction 150 pushes the leaflets 144, 146 apart at the opening 148.

Figure 7:
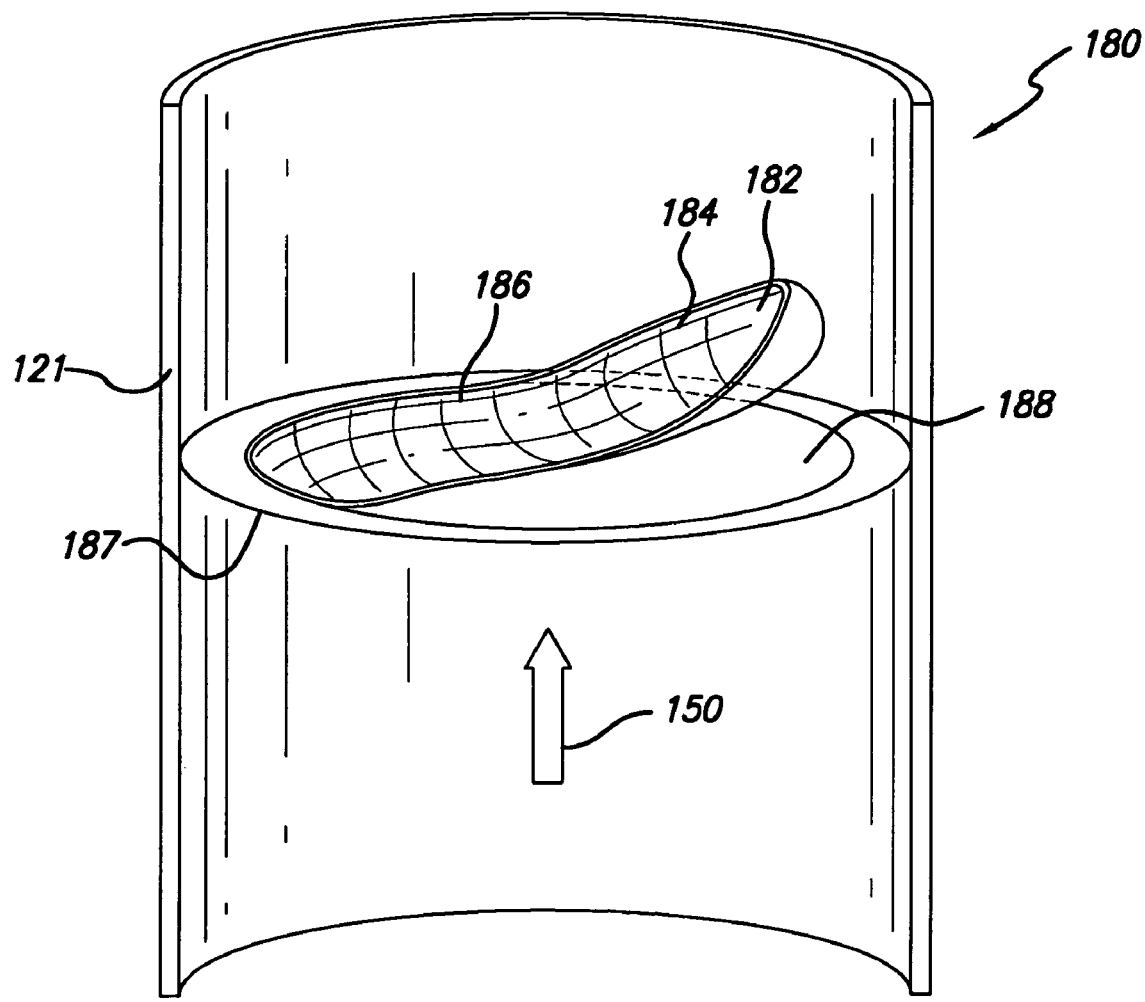
FIG. 7 illustrates an alternative embodiment of the present invention having a single flexible member.

An alternative embodiment of a valve device 180 is shown in FIG. 7, having a single leaflet 182 formed from a woven layer 10 including a first material 184 and a second material 186. The leaflet 182 contacts a portion of a support structure 187. The leaflet 182 moves between an open configuration shown in FIG. 7 when fluid flows in the first direction 150 through an opening 188 formed in the structure 187 and a closed configuration where the leaflet 182 covers the opening 188 to substantially prevent fluid flow in the second direction (not shown). The support structure 187 may also be formed from a woven layer 10.

Figure 8:
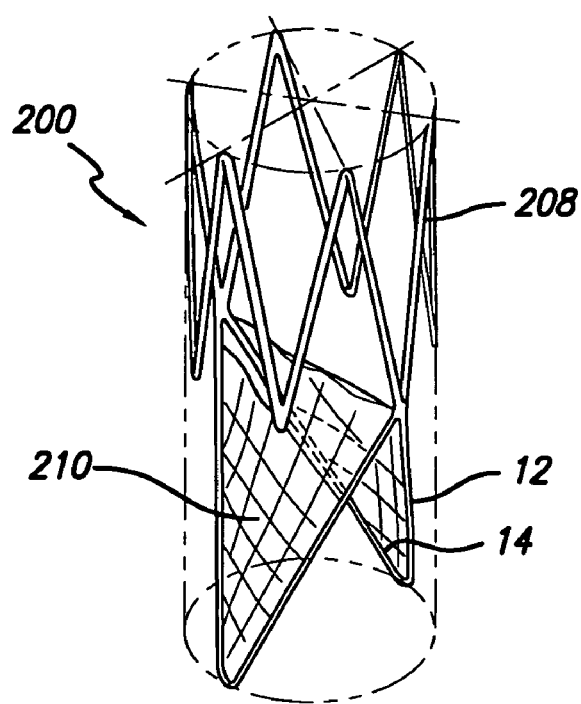
FIG. 8 illustrates an embodiment of a valve device of the present invention having a stent support structure.
Figure 9:
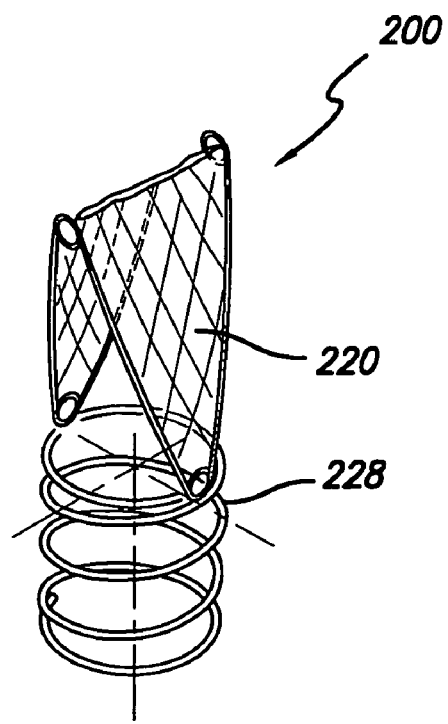
FIG. 9 illustrates an alternative embodiment of the valve device shown in FIG. 8.

A prosthetic valve device 200 is shown in FIGS. 8 and 9. The valve device 200 may include a support structure 208, 228 and a woven structure 210, 220 similar to the woven structure 10 described above. The support structure 208, 228 may be any support structure known in the art and need only provide a structure for attachment of a portion of the woven structure 210, 220. FIGS. 8 and 9 show examples of the support structure 208, 228. Alternatively, the woven structure 210, 220 may be attached internally to the support structure 208, 228. The support structure 208, 228 may provide a stenting function, i.e., exerts a radially outward force on the interior of the vessel in which the valve device 200 is implanted. The specific structure of the support structure 210, 220 will depend on several factors, including the vessel in which the valve device 200 is being implanted, the axial length of the treatment site, the inner diameter of the vessel, the delivery method, and others which will readily be understood by one of skill in the art. The support structure 208, 228 may be balloon- or self-expandable.

The support structure 208, 228 may also have a variety of configurations, including, braided strands, helically wound strands, ring members, consecutively attached ring members, tube members, and frames cut from solid tubes. The size of the support structure 208, 228 may depend on the delivery site of the valve device 200 and the support structure 208, 228 may be sized so that the second, expanded configuration is larger in diameter than an inner diameter of the vessel in which the valve device 200 will be implanted.

Examples of suitable support structures 208, 228 for use in the valve device of the present invention include those described in U.S. Pat. Nos. 6,508,833; 6,464,720; 6,231,598; 6,299,635; 4,580,568; and U.S. Patent Application Publication No. 2004/018658 A1, all of which are hereby incorporated by reference in their entirety.

In some embodiments, a portion of the valve device 100, 200 may include materials for orienting the device within a body lumen, such as a radiopaque region. For example, portions of the first material 12 or the second material 14 or both, or portions of the frame, can comprise a marker, or a delivery device comprising the leaflet can provide indicia relating to the orientation of the leaflet within the body vessel. The marker can be a radiopaque portion of the first material and the second material forming the leaflet that is detectable by imaging methods including X-ray, ultrasound, Magnetic Resonance Imaging and the like, or by detecting a signal from or corresponding to the marker. In other embodiments, the delivery device can comprise a leaflet with indicia relating to the orientation of the leaflet within the body vessel. In other embodiments, indicia can be located, for example, on a portion of a delivery catheter that can be correlated to the location of the leaflet within a body vessel. The addition of radiopacifiers (i.e., radiopaque materials) to facilitate tracking and positioning of the medical device may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film. Radiopaque, physiologically compatible materials include metals and alloys selected from the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biocompatible. Highly preferred is a platinum/tungsten alloy, e.g., 8% tungsten and the remainder platinum. The particular form and choice of material used for the implantable leaflet will depend on the desired application. Exemplary prosthetic valve devices and imageable materials are further described in U.S. Publication No. 2004/0167619, which is incorporated by reference herein in its entirety.

The woven structure 10 and the prosthetic valve device 100, 200 of the present invention may be delivered to a lumen of a body vessel by various techniques known in the art. By way of non-limiting example, the valve device 100, 200 may be delivered and positioned in the body vessel using a catheter. For delivery, the valve device 100, 200 may be placed in the unexpanded, first configuration to fit in the lumen of a delivery catheter. The catheter is then introduced into the body vessel and its tip positioned at a point of treatment within the body vessel. The valve device 100, 200 may then be delivered from the tip of the catheter to the point of treatment.

Once expelled from the catheter, the valve device 100, 200 may expand to the second, expanded configuration and engage the interior wall of the body vessel, preferably using structural features provided on the valve device. The valve-device 100, 200 may be self-expanding or expandable by a balloon of a balloon catheter as will be understood by one of skill in the art. Exemplary deployment apparatuses that may be used to deliver the valve devices of the present invention are described in U.S. Patent Application Publication Nos. 2004/0225322 and 2003/0144670, which are herein incorporated by reference in their entirety. Alternatively, rapid exchange catheters may be used, such as a rapid exchange delivery balloon catheter which allows exchange from a balloon angioplasty catheter to a delivery catheter without the need to replace the angioplasty catheter wire guide with an exchange-length wire guide before exchanging the catheters. Exemplary rapid exchange catheters that may be used to deliver the valve device of the present invention are described in U.S. Pat. Nos. 5,690,642; 5,814,061; and 6,371,961 which are herein incorporated by reference in their entirety.

The first material 12 and the second material 14 may be formed from a variety of materials known to one of skill in the art. The first material 12 and the second material 14 are preferably biocompatible or able to be made biocompatible. The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The first material 12 may be formed into sections suitable for weaving together with the second material 14. The size and shape of the first material 12 will depend on the factors listed above and the additional material woven together with the first material 12. By way of example, the first material 12 may be formed having length L determined by the position of the woven structure 10 in the patient and having a cross-sectional shape including, but not limited to, cylindrical, square, rectangular, oval, or triangular. Exemplary forms for the first material 12 include round rods having an outer diameter from about 0.0001 inches to about 0.250 inches, rectangular rods having a thickness of about 0.0001 inches to about 0.080 inches, tubes having an outer diameter of about 0.0001 inches to about 0.500 inches, and ribbons having a width from about 0.010 inches to about 0.500 inches and a thickness of about 0.0001 inches to about 0.040 inches. One of skill in the art will understand that additional dimensions and shapes are possible. Similar configurations may also be used for the second material 14.

In some embodiments, the actual material used for the first material 12 and the second material 14 is different. Alternatively, the second material 14 differs from the first material 12 in that the second material 14 includes different properties of the same actual material. For example, when the first material 12 and the second material 14 are formed from the same actual material, the sections of each material used for weaving may have different properties, such as thickness, size, shape, strength, flexibility, porosity, and the like.

In some embodiments, the first material 12 may be formed from materials that provide for a first, unexpanded configuration and a second expanded configuration for the woven structure 10. Examples of suitable materials for the first material 12 include, without limitation, stainless steel, shape memory alloys, such as titanium nickel (TiNi) alloys, titanium carbon-titanium nickel (TiC—TiNi) composite alloys, copper zinc (CuZn) alloys, copper zinc aluminum (CuZnAl) alloys, copper zinc gallium (CuZnGa) alloys, copper zinc tin (CuZnSn) alloys, copper zinc silicon (CuZnSi) alloys, iron platinum (FePt) alloys, tribological engineering materials or the like, platinum, gold or similar materials and/or superelastic materials, polymers, and composite materials. In some embodiments, the metallic surfaces are covered with a biocompatible, biostable, non-thrombogenic polymer layer. When a shape memory alloy is used to form the first material 12, the first material 12 may be shaped to form the leaflets of the valve device to provide a structure for the leaflet, for example, by providing a memory shape that biases the leaflets to an open or closed position as described above.

Examples of additional suitable materials that may be used in the present invention include natural materials, synthetic materials, and combinations of natural and synthetic materials. The biocompatible material may be, but is not required to be resorbable. As used herein, the term "resorbable" refers to the ability of a material to be absorbed into a tissue and/or body fluid upon contact with the tissue and/or body fluid. The contact can be prolonged, and can be intermittent. A number of resorbable materials are known in the art and any suitable material may be used. The material may also provide a matrix for the regrowth of autologous cells.

A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyesteramides, polyglutamic acid, poly-lysine, gelatin, fibrin, fibrinogen, casein, alginates and collagen.

Examples of biocompatible homo- or co-polymers suitable for use in the present invention include vinyl polymers including polyfumarate, polyvinylpyrolidone, polyvinyl alcohol, poly-N-(2-hydroxypropyl)-methacrylamide, polyacrylates, and polyalkylene oxalates.

Reconstituted or naturally-derived collagenous materials can be used in the present invention. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

Remodelable materials such as ECM materials can provide structural scaffolds into which cells from the host body can migrate and inhabit. Interactions between extracellular matrix components and cells can, in turn, mediate processes which are fundamental to migration, proliferation and differentiation during development. Without being limited to theory, it is believed that the ability of the matrix to bind molecules allows cells to secrete or sequester proteins, proteoglycans or other molecules, allowing cells to send chemical signals to surrounding cells. Cells could respond to these signals, for example, through adhesion, proliferation, migration, differentiation, metabolism or further secretion and sequestering of molecules. This is one type of mechanism by which cells can propagate the signal and possibly change the tissue properties in response to environmental change that initiated the chain of events during the remodeling process.

In addition to providing a destination for migration of various host body cells upon implantation within the body, remodelable materials often tend to contract during the remodeling process. Examples of recent studies of the contraction of remodelable matrix materials include: Feng Z, M. T. et al., "Measurements of the mechanical properties of contracted collagen gels populated with rat fibroblasts or cardiomyocytes." *J. Artif. Organs.* 6(3): 192-6 (2003); Phillips J. A. et al., "Fibroblasts regulate contractile force independent of MMP activity in 3D-collagen." *Biochem. Biophys. Res. Comm.* 312(3): 725-32 (2003); Zagai U. et al., "Platelets stimulate fibroblast-mediated ontraction of collagen gels," *Respir. Res.* 4(1): 13 (2003); Zaleskas J. M. et al., "Contractile forces generated by articular chondrocytes in collagen-glycosaminoglycan matrices." *Biomaterials* 25(7-8): 1299-308 (2004). These references are incorporated by reference herein. Typically, when cells such as fibroblasts, chrondrocytes, cardiomyocytes or others, migrate to and populate an implanted remodelable matrix material such as a collagen matrix, the cells can undergo a variety of changes when activated, including establishing a contractile mechanism. Without being limited to theory, some investigations have suggested that platelets and platelet lysates, such as platelet-derived growth factor (PDGF) and transforming growth factor-beta (TGF-beta), may partially mediate this activation of a contractile mechanism. The cellular contractile mechanism, also called cell-mediated contraction, has been shown to result in contraction of collagen gels in vitro and may play an active role in the remodeling of extracellular matrix and extracellular matrix contraction. Remodelable matrix materials, such as ECM material, can have a three-dimensional structure capable of translating mechanical strain of the tissue to the cells through cell attachment points called ligands, which link the cells to the matrix. "Mechanical strain" refers to strain caused by, resulting from, or relating to a process that involves a physical, as opposed to a chemical, change. The structure and consistency of the extracellular matrix material allow translation of contractile and tensile loads in multiple axes to the cells as the loads are imparted on the tissue.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al. *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Small intestine submucosa (SIS) is an example of an ECM that may be used as the second material 14. SIS may be provided as a sheet and woven together with the first material 12 as described above. Alternatively, the SIS may be cut into pieces, be shredded or ground into small sized bits. The smaller pieces may be sprayed, formed or cast onto a mandrel of the appropriate shape and size for the structure desired. The cast may then be dried or hardened and the casting form removed, leaving the SIS in the shape of the form. The first material 12 may be embedded into the SIS material as it is being formed on the mandrel resulting in a partially woven first material 12 and second material 14 forming the woven structure 10. Alternatively, the first material 12 may be woven into the formed SIS material.

The second material 14 when formed from SIS material or the like, may also be ground or shredded into fine, fibrous particles or strands which may then be made into fibers, including monofilaments, yarns, threads, braids, or bundles of fibers. The SIS fibers may be woven with the first material 12 to form the woven structure 10. The SIS material may also be cut into strips from its normally occurring sheet form. The SIS strips may be used to weave together with the first material 12 to form the woven structure 10.

The second material 14, preferably formed from SIS, and the first material 12 may then be subjected to pressure, for example, but not limited to, vacuum bagging, tape wrapping or suitable methods to compress the second material together during curing to provide the second material with more uniform thickness and porosity.

In another aspect, the woven material 10 can be formed from a shape-retaining gelled form of vertebrate submucosa. The term "shape retaining gel" is defined herein to refer to a gel that holds its three dimensional molded shape (i.e. no significant change in the height, length or width) in a hydrated environment for at least one hour at 20 C. after removal from the mold and placement on a flat surface without any other support. The method of forming the shape retaining gel of the present invention is described in published US Patent Application No. US2003/0012823, filed Jan. 16, 2003, and incorporated herein by reference. Advantageously, the method enables the formation of a translucent, shape retaining gel from a complex extracellular matrix that can be configured to form a component of a woven material, or can be adhered to a woven material to form a leaflet. The shape retaining gelled submucosa can be produced by a method comprising the steps of enzymatically treating warm-blooded vertebrate submucosa to produce a hydrolysate of vertebrate submucosa having multiple hydrolyzed submucosa components, fractionating the hydrolysate to remove at least a portion of the hydrolysate components and gelling the fractionated hydrolysate. Typically the submucosa material is first comminuted before enzymatic digestion of the submucosa by tearing, cutting, grinding, or shearing the harvested submucosal tissue and then lyophilizing the material to produce a powder. The submucosa powder can thereafter be hydrated with water or buffered saline to form a submucosal fluid of liquid or paste-like consistency. In one preferred embodiment the submucosal tissue is comminuted by freezing and pulverizing the submucosa under liquid nitrogen in an industrial blender. The submucosa is enzymatically digested for a sufficient time to produce a hydrolysate of submucosa components.

SIS is commercially available from Cook Biotech, West Lafayette, Ind. The porosity of the woven structure 10 preferably does not allow fluid flow therethrough. Additional layers or coatings may be applied to the woven structure 10 after the woven structure 10 is made. The coating may include growth inhibiting compounds, growth promoting compounds, antibiotics, anti-inflammatory agents and the like.

Materials used to form the valves of the present invention or portions thereof may be formed with a variety of materials, including biocompatible polyurethanes. One example of a biocompatible polyurethane is THORALON (THORATEC, Pleasanton, Calif.). As described in U.S. Pat. Nos. 4,675,361 and 6,939,377, both of which are incorporated herein by reference. THORALON is a polyurethane base polymer blended (referred to as BPS-215) with a siloxane containing surface modifying additive (referred to as SMA-300). The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates, pore forming agents or inorganic salts. Preferably the particulate is insoluble in the solvent. Examples of solvents include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water f. or the extraction, for example water at a temperature of about 60° C. The resulting pore diameter can be substantially equal to the diameter of the salt grains.

The porous polymeric sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and U.S. Patent Application Publication No. 2003/0149471 A1, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes may also be employed. These include polyurethane ureas that preferably include a soft segment and include a hard segment formed from a diisocyanate and diamine. For example, polyurethane ureas with soft segments such as polytetramethylene oxide, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic or a mixture of aliphatic and aromatic moieties. Examples of diisocyanates include tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

Biocompatible polyurethanes modified with cationic, anionic and aliphatic side chains may also be used. See, for example, U.S. Pat. No. 5,017,664.

Other biocompatible polyurethanes include: segmented polyurethanes, such as BIOSPAN; polycarbonate urethanes, such as BIONATE; and polyetherurethanes such as ELASTHANE; (all available from POLYMER TECHNOLOGY GROUP, Berkeley, Calif.).

Other biocompatible polyurethanes include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible polyurethanes may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

Additional examples of suitable materials for portions of the valve 10 include, without limitation, stainless steel (such as 316 stainless steel), nickel titanium (NiTi) alloys, e.g., Nitinol, other shape memory and/or superelastic materials, MP35N, gold, silver, a cobalt-chromium alloy, tantalum, platinum or platinum iridium, or other biocompatible metals and/or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhidride, polyether sulfone, polycarbonate, polypropylene, high molecular weight polyethylene, polytetrafluoroethylene, expanded polytetrafluoroethylene or other biocompatible polymeric material, or mixture of copolymers thereof, or stainless steel, polymers, and any suitable composite material.

As described above for FIG. 4, the third material 34 may be woven together with the first and second materials 12 and 14. The third material may be any material known to one of skill in the art suitable for implantation into a recipient, including, but not limited to, the materials described above with reference to the first material 12 and the second material 14.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. The scope of the invention is defined by the appended claims, and all devices that come within the meaning of the claims, either literally or by equivalence, are intended to be embraced therein.

The invention claimed is:

1. A prosthetic valve for implantation in a body vessel, said prosthetic valve having a lengthwise axis and comprising:
    at least one flexible member movable between a first position that permits fluid flow in a first direction and a second position that substantially prevents fluid flow in a second direction, the at least one flexible member formed of a woven structure having a surface and an outer edge, the woven structure comprising a continuous weave of first and second materials forming the surface;
    the first material including multiple fibers interwoven with the second material, wherein the multiple fibers extend from the continuous weave along the outer edge of the flexible member to form a structure perimeter formed only of the first material and defining the perimeter of the woven structure; and
    a plurality of extensions formed of the first material, each extension of the plurality of extensions extending outward from the structure perimeter relative to said lengthwise axis of said prosthetic valve and adapted for engaging said body vessel;
    wherein said prosthetic valve has a first, unexpanded configuration and a second, expanded configuration.

2. The prosthetic valve of claim 1, wherein the second material comprises a remodelable material.

3. The prosthetic valve of claim 1, wherein the second material comprises an extracellular matrix material (ECM).

4. The prosthetic valve of claim 1 wherein the second material comprises a synthetic material.

5. The prosthetic valve of claim 1 wherein the first material comprises a shape memory alloy.

6. The prosthetic valve of claim 5 wherein the shape memory alloy provides a memory shape for the flexible member in the expanded configuration.

7. The prosthetic valve of claim 1 wherein the woven structure comprises a continuous weave of first, second and third materials along the surface.

8. The prosthetic valve of claim 1 further comprising an opening defined in the woven structure.

9. The prosthetic valve of claim 8, wherein the at least one flexible member comprises a pair of flexible members; and
    wherein the pair of flexible members forms a member contact area when the flow is in the second direction.

10. The prosthetic valve of claim 1, further comprising a support structure operably connected to the at least one flexible member.

11. The prosthetic valve of claim 1, wherein the second material is provided as a sheet of material and the first material is at least partially woven into the sheet.

12. The prosthetic valve of claim 1, wherein the first material comprises a shape memory alloy and the second material comprises a remodelable material.

13. The prosthetic valve of claim 12, wherein the first material comprises a titanium nickel alloy.

14. The prosthetic valve of claim 12, wherein the second material comprises an extracellular matrix material (ECM).

15. The prosthetic valve of claim 14, wherein the ECM comprises small intestine submucosa (SIS).

16. The prosthetic valve of claim 12, wherein the first material comprises a titanium nickel alloy and the second material comprises an extracellular matrix material (ECM).

17. The prosthetic valve of claim 1, wherein the woven structure comprises a mesh formed from a uniform weave of the first material and the second material.

18. The prosthetic valve of claim 1, wherein the woven structure comprises a mesh formed from a non-uniform weave of the first material and the second material.

* * * * *